(12) United States Patent
Palmer et al.

(10) Patent No.: US 9,255,053 B2
(45) Date of Patent: Feb. 9, 2016

(54) TREATMENT OF BISPHENOL-A RESIDUE STREAMS

(75) Inventors: David P. Palmer, Katy, TX (US); Steven D. Evitt, Somerville, MA (US); Stephen W. Fetsko, Hingham, MA (US); Chung-Ming Chi, Needham, MA (US)

(73) Assignee: BADGER LICENSING LLC, Boston, MA (US)

( * ) Notice: Subject to any disclaimer, the term of this patent is extended or adjusted under 35 U.S.C. 154(b) by 446 days.

(21) Appl. No.: 13/487,872

(22) Filed: Jun. 4, 2012

(65) Prior Publication Data

US 2012/0310014 A1 Dec. 6, 2012

Related U.S. Application Data

(60) Provisional application No. 61/493,675, filed on Jun. 6, 2011.

(51) Int. Cl.
| | | |
|---|---|---|
| C07C 37/72 | (2006.01) | |
| C07C 37/52 | (2006.01) | |
| C07C 37/20 | (2006.01) | |
| C07C 45/51 | (2006.01) | |

(52) U.S. Cl.
CPC ............... *C07C 37/52* (2013.01); *C07C 37/20* (2013.01); *C07C 37/72* (2013.01); *C07C 45/51* (2013.01)

(58) Field of Classification Search
CPC ............................ C07C 41/42; C07C 43/23
USPC .................. 568/749, 751, 761, 919, 762
See application file for complete search history.

(56) References Cited

U.S. PATENT DOCUMENTS

| | | | |
|---|---|---|---|
| 3,075,015 A * | 1/1963 | Meyer et al. ............. | 568/324 |
| 6,191,316 B1 | 2/2001 | Fennhoff et al. | |
| 8,431,749 B2 * | 4/2013 | Palmer et al. ............ | 568/386 |
| 2005/0240065 A1 * | 10/2005 | Blaschke et al. .......... | 568/810 |
| 2006/0004234 A1 | 1/2006 | Prein et al. | |

FOREIGN PATENT DOCUMENTS

| | | |
|---|---|---|
| EP | 0112615 A2 | 7/1984 |
| GB | 795236 | 5/1958 |

OTHER PUBLICATIONS

Adschiri T., Shibata R., Arai, K., Sekiyu Gakkasishi—"Phenol Recovery by BPA Tar Hydrolysis in Supercritical Water", vol. 40, No. 4, 1997, p. 291-297.
International Search Report and Written Opinion issued on Aug. 29, 2012 in a corresponding PCT/US2012/040676.

* cited by examiner

*Primary Examiner* — Sudhakar Katakam
*Assistant Examiner* — Pancham Bakshi
(74) *Attorney, Agent, or Firm* — Roberts Mlotkowski Safran & Cole, P.C.

(57) ABSTRACT

In a method of treating a residue stream from the production of bisphenol-A, the residue stream is contacted with an aqueous solution of a base under conditions effective to hydrolyze at least part of said residue stream into acetone and phenol and produce an effluent stream. Acetone is recovered from the effluent stream to produce a phenol-containing mixed phase stream which is substantially free of acetone and which contains water and unhydrolyzed heavy organic compounds. The phenol-containing mixed phase stream is then treated with a water-immiscible organic solvent to extract phenol and unhydrolyzed heavy organic compounds into said solvent and produce an organic phase containing the solvent, phenol and unhydrolyzed heavy aromatic compounds and an aqueous phase with reduced concentrations of phenol and unhydrolyzed heavy organic compounds. At least part of the phenol and the organic solvent are subsequently recovered from the organic phase.

10 Claims, 3 Drawing Sheets

TREATMENT OF BISPHENOL-A RESIDUE STREAMS

FIELD

The present invention relates to treatment of bisphenol-A residue streams.

BACKGROUND

Bisphenol-A (4,4'-dihydroxy-2,2-diphenylpropane or BPA) is produced by condensation of acetone with an excess of phenol in the presence of an acidic catalyst or a cation-exchange resin. The crude product, in addition to the desired bisphenol-A and unreacted phenol, contains unwanted by-products, such as bisphenol-A isomers, trisphenols and other higher molecular weight materials. The bisphenol-A is normally separated from the crude product by a single or a series of crystallization steps, leaving a mother liquor stream enriched in unwanted by-products, a portion of which stream is removed to purge unwanted by-products from the process. Alternately, the bisphenol-A may be separated from the crude product by a single or series of distillation steps, which also creates a stream enriched in unwanted by-products, a portion of which is removed. The removed stream may contain unreacted phenol and bisphenol-A as well as the unwanted by-products. Phenol is typically recovered from the removed stream by distillation, normally vacuum distillation, to create a residue stream concentrated in unwanted heavies which is purged from a BPA manufacturing process.

There is substantial prior art describing methods for recovering phenol and isopropenyl phenol from such residue streams to improve the economic performance of the overall BPA manufacturing process. One such method is described in U.S. Pat. No. 6,191,316 and involves addition of catalytic amounts of base at elevated temperature under vacuum to decompose BPA isomers, trisphenols and other by-products into phenol and isopropenyl phenol followed by addition of catalytic amounts of acid at elevated temperature under vacuum to recover phenol.

In addition, there is substantial prior art describing methods for recovering phenol and acetone from BPA and BPA residue streams. One such method involves hydrolysis of BPA and BPA residues purged from a BPA manufacturing process in the presence of water at supercritical or near-supercritical temperatures and pressures (see, "Phenol Recovery by BPA Tar Hydrolysis in Supercritical Water", Adschiri T., Shibata R., Arai, K., Sekiyu Gakkasishi, Vol 40, No. 4, 1997, p. 291-297).

Moreover, hydrolysis of BPA and BPA residue has been shown to occur at subcritical temperatures and pressures in the presence of an aqueous solution of ammonia, alkali-metal and alkaline earth metal hydroxides and carbonates to produce phenol and acetone which can then be recovered (see U.S. Pat. No. 3,075,015). In this process, the concentrated heavies are reacted with sodium hydroxide solution or other basic solution to convert the p,p-BPA and other compounds back to phenol and acetone. The acetone is recovered in a distillation column and the phenol is recovered by neutralization followed by steam distillation. Phenol and acetone yields using hydrolysis are substantially improved compared to methods using catalytic decomposition in the absence of water.

However, the '015 patent is silent as to subsequent treatment or disposition of the remaining aqueous mixture or the unhydrolyzed heavies. Therefore, to achieve economic benefit from hydrolysis of the BPA isomers and impurities in the residue stream, a solution is required to efficiently recover and recycle acetone and phenol from hydrolysis of the concentrated heavies to the BPA manufacturing process, to efficiently dispose of the resulting aqueous mixture, and to efficiently separate the unhydrolyzed heavy organic compounds from the aqueous mixture. The present invention seeks to provide such a solution.

SUMMARY

Accordingly, the invention resides in one aspect in a method of treating a residue stream from the production of bisphenol-A, the method comprising:

(a) contacting the residue stream with an aqueous solution of a base under conditions effective to hydrolyze at least part of said residue stream into acetone and phenol and produce an effluent stream;

(b) recovering acetone from the effluent stream to produce a phenol-containing mixed phase stream which is substantially free of acetone and which contains water and unhydrolyzed heavy organic compounds;

(c) treating the phenol-containing mixed phase stream with a water-immiscible organic solvent to extract phenol and unhydrolyzed heavy organic compounds into said solvent and produce an organic phase containing said solvent, phenol and unhydrolyzed heavy aromatic compounds and an aqueous phase with reduced concentrations of phenol and unhydrolyzed heavy organic compounds; and (d) recovering at least part of the phenol and the organic solvent from the organic phase.

Conveniently, acetone is recovered from the effluent stream in (b) by distillation. Generally, at least part of the acetone recovered in (b) is recycled to the production of bisphenol-A.

Conveniently, the water-immiscible organic solvent is selected from cumene, toluene, a mixture of cumene and alpha methyl styrene (AMS), ethers, ketones, and acetate esters.

In one embodiment, at least a portion of the aqueous phase produced in (c) is recycled to the contacting step (a).

In another embodiment, the phenol-containing mixed phase stream from (b) is combined with an acid to reduce the pH of said stream to about 2 to about 8, such as about 5 to about 7, prior to said treating step (c).

In one embodiment, the recovering (d) is effected by one or more distillation steps. Conveniently, at least part of the phenol recovered in (d) is recycled to the production of bisphenol-A and at least part of the solvent recovered in (d) is recycled to the treating (c).

In a further aspect, the invention resides in a method of producing bisphenol-A, the method comprising:

(a) condensing acetone with a molar excess of phenol in the presence of a catalyst under conditions to produce a product stream comprising bisphenol-A and isomers thereof, unreacted phenol, trisphenols and other heavy aromatic compounds;

(b) recovering part of the bisphenol-A and unreacted phenol from said product stream to leave a residue stream comprising unreacted phenol, bisphenol-A and isomers thereof, trisphenols, and other heavy aromatic compounds;

(c) contacting the residue stream with an aqueous solution of a base under conditions effective to hydrolyze at least part of said residue stream into acetone and phenol and produce an effluent stream;

(d) recovering acetone from the effluent stream to produce a phenol-containing mixed phase stream which is substantially free of acetone and which contains water and unhydrolyzed heavy organic compounds;

(e) treating the phenol-containing mixed phase stream with a water-immiscible organic solvent to extract phenol and unhydrolyzed heavy organic compounds into said solvent and produce an organic phase containing said solvent, phenol and unhydrolyzed heavy aromatic compounds and an aqueous phase with reduced concentrations of phenol and unhydrolyzed heavy organic compounds; and (f) recovering at least part of the phenol and the organic solvent from the organic phase, and (g) purging at least part of the remaining unhydrolyzed heavy organic compounds.

DETAILED DESCRIPTION OF THE EMBODIMENTS

Figure 1:
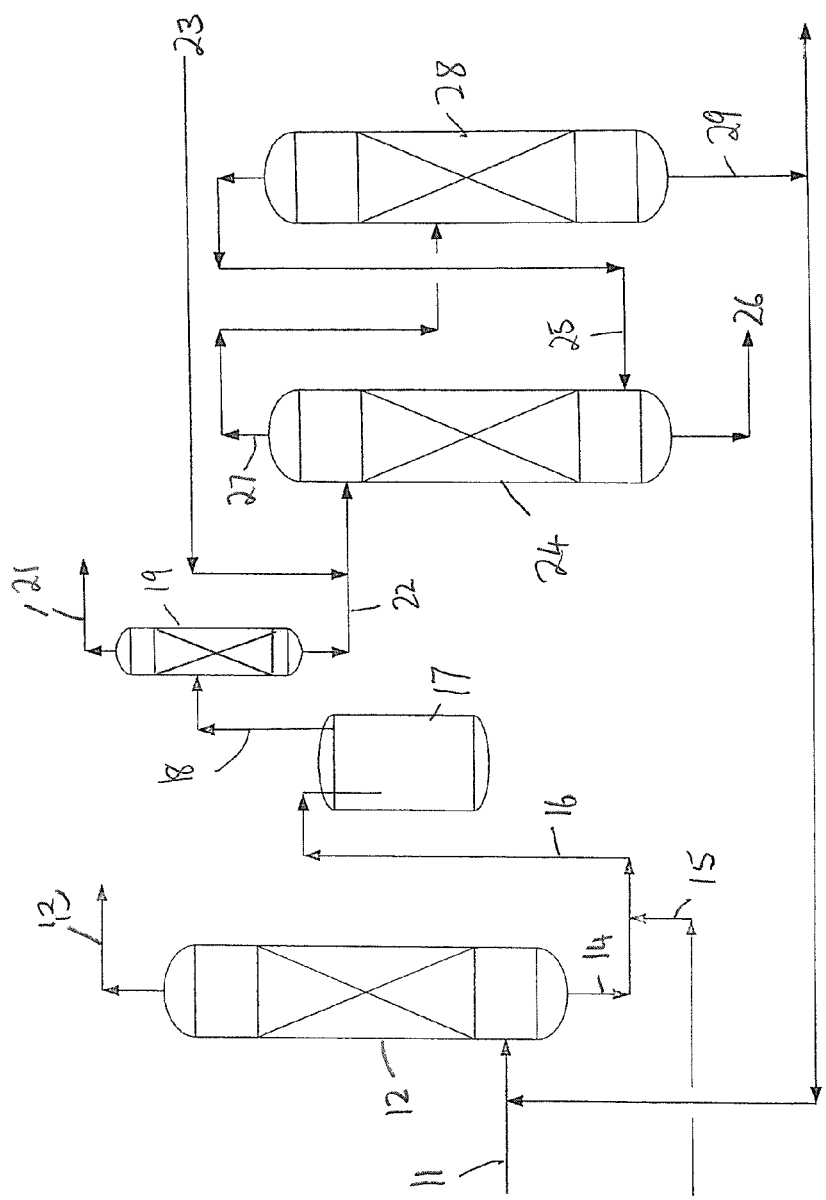
FIG. 1 is a flow diagram of a method according to a first example of the invention for recovering phenol and acetone from a BPA residue stream.

Described herein is an improved process for recovering phenol and acetone from a residue stream from the production of bisphenol-A.

The manufacture of bisphenol-A (BPA) generally involves reacting acetone with a stoichiometric excess of phenol in the presence of an acid catalyst. The phenol/acetone molar ratio is usually in the range from 3 to 30, typically from 5 to 20. The reaction is typically carried out at a temperature of about 50 to about 100° C. under a pressure of from atmospheric pressure to about 600 kPa.

As the catalyst, usually strong mineral acids or strongly acidic cation exchange resins such as sulfonic acid type resins, including those partially neutralized with a sulfur-containing amine compound are used. As the sulfur-containing amine compound, ordinary promoters used for the synthesis of bisphenol A such as, for example, 2-(4-pyridyl) ethanethiol, 2-mercaptoethylamine, 3-mercaptopropylamine, N,N-dimethyl-3-mercaptopropylamine, N,N-di-n-butyl-4-mercaptobutylamine, and 2,2-dimethylthiazolidine can be used. Such a promoter is used in an amount of usually 2 to 30 mol %, such as 5 to 20 mol % based on the acid group (sulfonic group) in the acid ion exchanger.

The condensation reaction of the phenol and acetone is typically conducted in a fixed bed continuous flow system or a suspended bed batch system. In the case of the fixed bed flow system, the liquid space velocity of the mixture of the raw materials supplied to the reactor is usually 0.2 to 50 hr$^{-1}$. In the case of the suspended bed batch system, the amount of the strongly acid ion exchange resin used, although variable depending on the reaction temperature and pressure, is usually 20 to 100% by weight based on the mixture of the raw materials. The reaction time is usually 0.5 to 5 hours.

In addition to the desired bisphenol-A, the effluent from the condensation reaction comprises reaction-generated water, unreacted acetone, unreacted phenol, and a variety unwanted by-products, such as bisphenol-A isomers (for example, 2-(4-hydroxyphenyl)-2-(2-hydroxyphenyl)propane or o,p-BPA), trisphenol (see formula I below), isopropenyl phenol (IPP) dimers (see formulae IIa, IIb and IIc below) and hydroxyphenyl chromans (see formulae IIIa and IIIb below), substituted xanthenes and more highly condensed compounds having three or more phenyl rings in the molecular framework. Collectively, the IPP dimers, hydroxylphenyl chromans, indanes, xanthenes and more highly condensed compounds are termed as "BPA heavies."

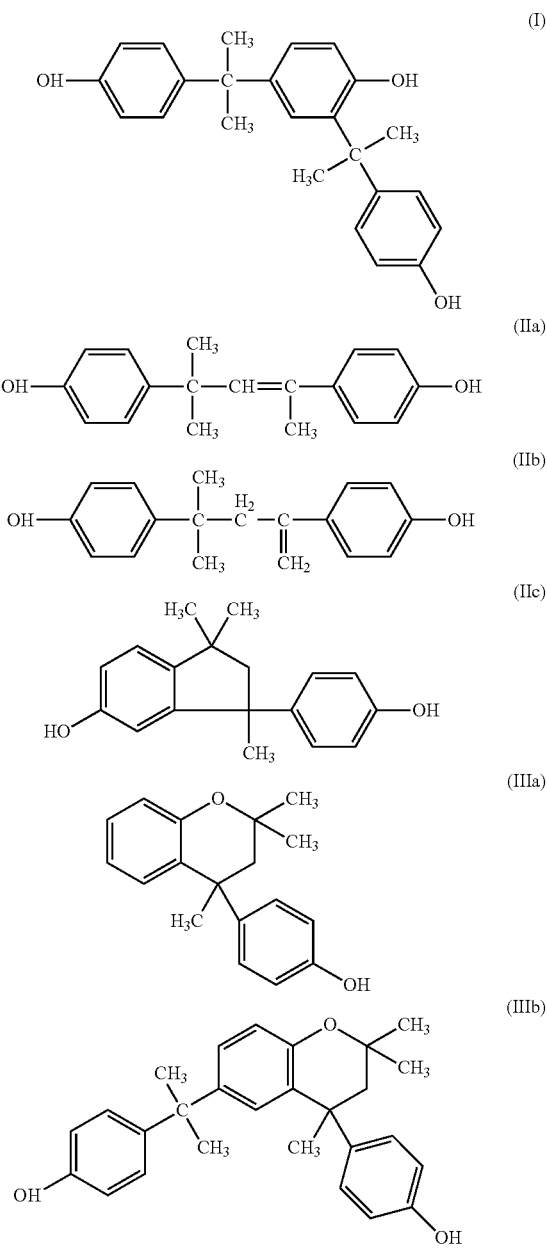

These by-products, as well as the water, phenol and acetone, impair the suitability of the BPA for the production of polymers and must be separated from the condensation effluent. For the production of polycarbonate in particular, high demands are made on the purity of the raw material BPA.

The purification of the BPA is carried out by a multi-stage cascade of suitable purification processes such as, for example, suspension crystallization, melt crystallization, distillation and/or desorption. After separation of the BPA product, these processes leave a mother liquor which contains BPA, water, unreacted phenol and possibly unreacted acetone, and which also contains the above-mentioned by-products. Typically, this stream of mother liquor is recycled to the condensation reaction. In order to maintain the catalytic activity of the acidic ion exchanger, all or some of the water that has formed is removed beforehand by distillation, together with any unreacted acetone that is still present. The dewatered mother liquor so obtained is supplemented with additional phenol and acetone and fed back into the condensation unit.

Such a recycle procedure has the disadvantage that the by-products of the BPA preparation become concentrated in the circulating stream and can adversely affect the purity of the final BPA product and may lead to deactivation of the catalyst system. In order to avoid excessive concentration of the by-products in the circulating stream, a portion of the mother liquor mixture must be discharged from the system. The discharge is typically effected by removing a portion of the mother liquor from the circulating stream, often after distillation to remove water of reaction, unreacted acetone and part of the unreacted phenol. The composition of the mother liquor at this point, and accordingly also the composition of the discharge, typically comprises from 60 to 90 wt. % phenol, from 6 to 20 wt. % BPA and from 3 to 15 wt. % BPA isomers and heavier by-products. Since this discharge stream contains significant quantities of phenol and other useful products, the discharge is a valuable process stream which is subjected to further processing.

Further processing of the discharge stream initially involves distilling off the phenol to a residual content of less than 20 wt %, such as less than 10 wt. %, especially less than 5 wt. %, even less than 1 wt. %, normally by vacuum distillation, leaving a heavy residue stream comprising <10 wt. % phenol, about 45 to about 55 wt. % BPA and isomers thereof, and about 45 to about 55 wt. % BPA heavies.

After removal of the phenol, the heavy residue stream is contacted with water and a source of hydroxyl ions under conditions effective to hydrolyze at least part of the residue stream to phenol and acetone. Suitable conditions for hydrolysis of the residue stream include a temperature of about 150° C. to about 300° C., such as about 180° C. to about 260° C., at a pressure sufficient to keep the water substantially in the liquid phase at said temperature. Suitable pressures are from about 2.7 MPa to about 4.2 MPa.

The source of hydroxyl ions used to catalyze the hydrolysis reaction can be an aqueous solution of ammonia and/or an alkali metal hydroxide and/or an alkaline earth metal hydroxide, with sodium hydroxide being preferred. The amount of the hydroxyl ion source added to the residue stream is controlled so that the molar ratio of hydroxyl ions to hydroxyphenyl groups in the residue stream is from about 0.3:1 to about 0.9:1, such as from about 0.4:1 to about 0.7:1. Thus it is found that advantageous phenol and acetone recoveries can be achieved within these ranges, whereas increasing the hydroxyl/hydroxyphenyl molar ratio above these ranges achieves little or no improvement in recovery and increases caustic usage.

The amount of water added to the residue stream is normally adjusted so that the weight ratio of water to the sum of BPA isomers, trisphenols and other aromatic heavies in the feed stream is greater than or equal to 2:1, since at water/heavies ratios below 2 it is found that the recovery of phenol and acetone in the hydrolysis reaction is decreased. Generally, the weight ratio of water to the sum of BPA isomers, trisphenols and other aromatic heavies in the feed stream is from about 2:1 to about 10:1.

The duration of the hydrolysis reaction is generally determined by the degree of phenol and acetone recovery desired. In particular, it is found that advantageous recovery rates in excess of 70%, even in excess of 80%, can be achieved with reaction times less than 4 hours, such as from about 2 to about 3 hours. Residence times above these values generally lead to little increase in phenol and acetone recovery. In this respect, the product recoveries are defined as the number of moles of phenolic rings or acetone moieties in the feed minus the number the moles of hydroxyphenyl or acetone moities in the product divided by the number the moles of hydroxyphenyl or acetone moieties in the feed. For both recoveries, the number of moles of phenol and acetone in the feed are excluded from the calculation.

The effluent from the hydrolysis reaction is composed of a mixture of acetone, phenol, water and unhydrolyzed heavy organic compounds and is initially passed to an acetone recovery section. Acetone recovery is conveniently achieved by fractionating the hydrolysis effluent to separate an acetone-containing overhead fraction and produce a phenol-containing mixed phase bottoms stream which is substantially free of acetone and which contains water and unhydrolyzed heavy organic compounds. Typically, the bottoms stream contains less than 1 wt %, preferably less than 0.5 wt %, more preferably less than 0.25 wt % acetone.

The bottoms stream is then fed to a solvent extraction unit where it is treated with a water-immiscible organic solvent. Suitable solvents include cumene, toluene, a mixture of cumene and alpha methyl styrene (AMS), ethers, such as methyl tert-butyl ether (MTBE), ethyl tert-amyl ether and diisopropyl ether, ketones, such as methyl ethyl ketone and methyl isobutyl ketone, and acetate esters, such as propyl acetate, butyl acetate, amyl acetate, and hexyl acetate.

The solvent extracts phenol and unhydrolyzed heavy organic compounds from the bottoms stream to produce an organic phase containing the solvent, phenol and unhydrolyzed heavy aromatic compounds and an aqueous phase with reduced concentrations of phenol and unhydrolyzed heavy organic compounds. The organic and aqueous phases are separately removed from the solvent extraction unit and subjected to further treatment as will be described in more detail below. In particular, the organic phase is passed to a solvent recovery section, normally a distillation column, where the solvent is removed and recycled to solvent extraction unit. Concurrent or subsequent distillation may be employed to separate phenol from the unhydrolyzed heavy aromatic compounds, at least part of which are then purged.

The invention will now be more particularly described with reference to the accompanying drawings, wherein like reference numerals designate like components.

Referring to FIG. 1, in a first example of the invention, the mother liquor remaining after removal of BPA from the product of the condensation reaction of phenol and acetone is fed by line 11 to a phenol recovery column 12, where most of the phenol is removed as overhead stream 13. The bottoms 14 from the column 12 is composed mainly of BPA isomers, trisphenol, isopropenyl phenol (IPP) dimers and other heavy organic compounds and is combined with an aqueous caustic stream 15 and fed via line 16 to a hydrolysis reactor 17.

The heavy organic compounds in the bottoms stream 14 are partially hydrolyzed back to acetone and phenol in reactor 17 so that the effluent from the reactor is a mixture composed mainly of acetone, phenol, water and unhydrolyzed heavy organic compounds. The effluent is passed by line 18 to an acetone recovery column 19 where the effluent is separated into an acetone-containing overhead stream 21 and a phenol-containing mixed phase bottoms stream 22 which is substantially free of acetone and which contains water, phenol, phenate and unhydrolyzed heavy organic compounds. The bottoms stream 22 is neutralized with acid, such as sulfuric acid, introduced through line 23 to convert the phenate to phenol and the resultant neutralized stream is fed to a solvent extraction unit 24.

The neutralized bottoms stream flows through the solvent extraction unit 24 countercurrent to an immiscible solvent, which is added to the unit 24 via line 25. The immiscible solvent extracts phenol and unhydrolyzed heavy organic compounds from the bottoms stream to produce an organic phase containing the solvent, phenol and unhydrolyzed heavy aromatic compounds and an aqueous phase with substantially reduced concentrations of phenol and unhydrolyzed heavy organic compounds. The aqueous phase is removed from the solvent extraction unit 24 via line 26 and is sufficiently low in phenol and unhydrolyzed heavy organics that it is suitable for secondary waste water treatment. The organic phase is removed from unit 24 by line 27 and is fed to a solvent recovery column 28. The organic phase is fractionated in the column 28 to separate the solvent which is removed as overhead and recycled via line 25 to the solvent extraction unit 24. This leaves a bottoms fraction rich in phenol which is removed from the solvent recovery column 28 via line 29 and is recycled to the column 12 for recovery of the phenol. Part of the bottoms must be purged to avoid build-up of heavy organic compounds in the recycle stream 29.

Figure 2:
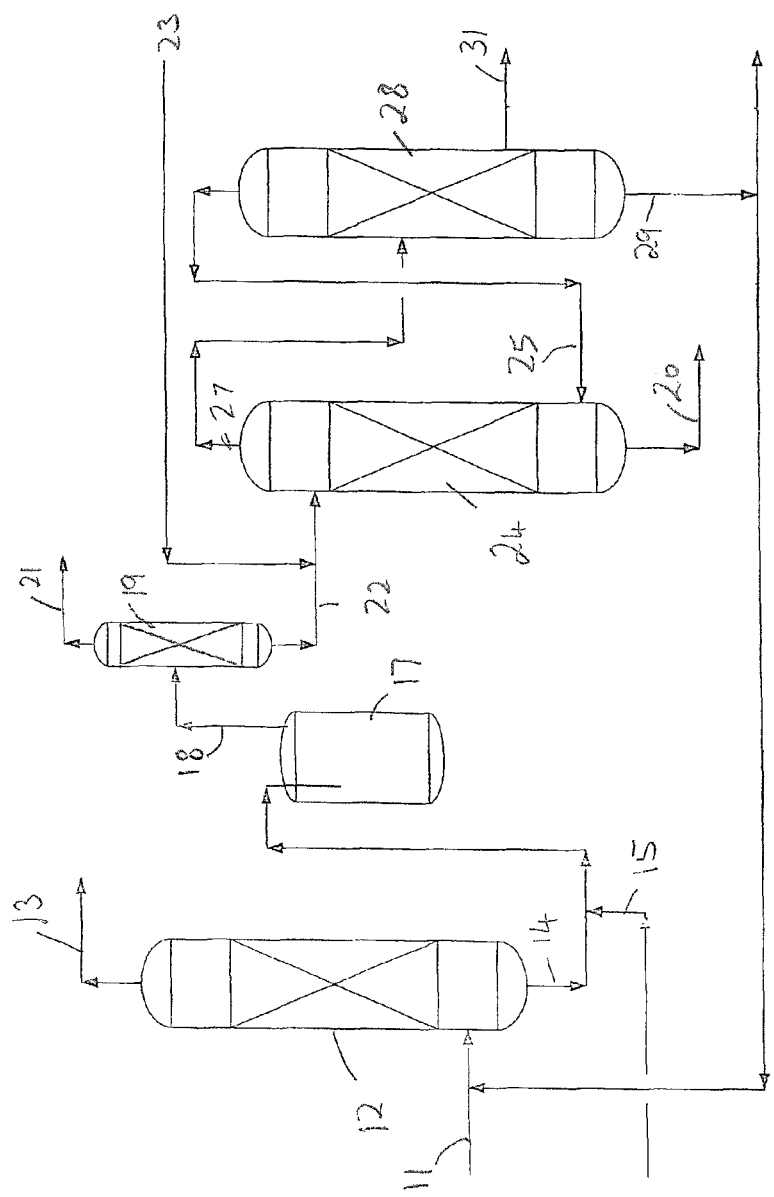
FIG. 2 is a flow diagram of a method according to a second example of the invention for recovering phenol and acetone from a BPA residue stream.

A second and similar example is shown in FIG. 2, in which provision is made for recovering phenol that reduces the loss of phenol in the purge. Thus, referring to FIG. 2, in the second example phenol is removed from the solvent recovery column 28 as a side stream 31 so that the bottoms exiting the column 28 via line 29 is composed mainly of unhydrolyzed heavy organic compounds. The phenol recovered from side stream 31 can then be recycled to the BPA manufacturing process. At least a portion of bottom stream 29 is transferred to an incinerator, industrial boiler or other disposal mechanism. Depending on plant operation, it may not be necessary to purge the entire bottoms stream. The remaining portion of the bottoms stream 29 may be recycled to the column 12.

Figure 3:
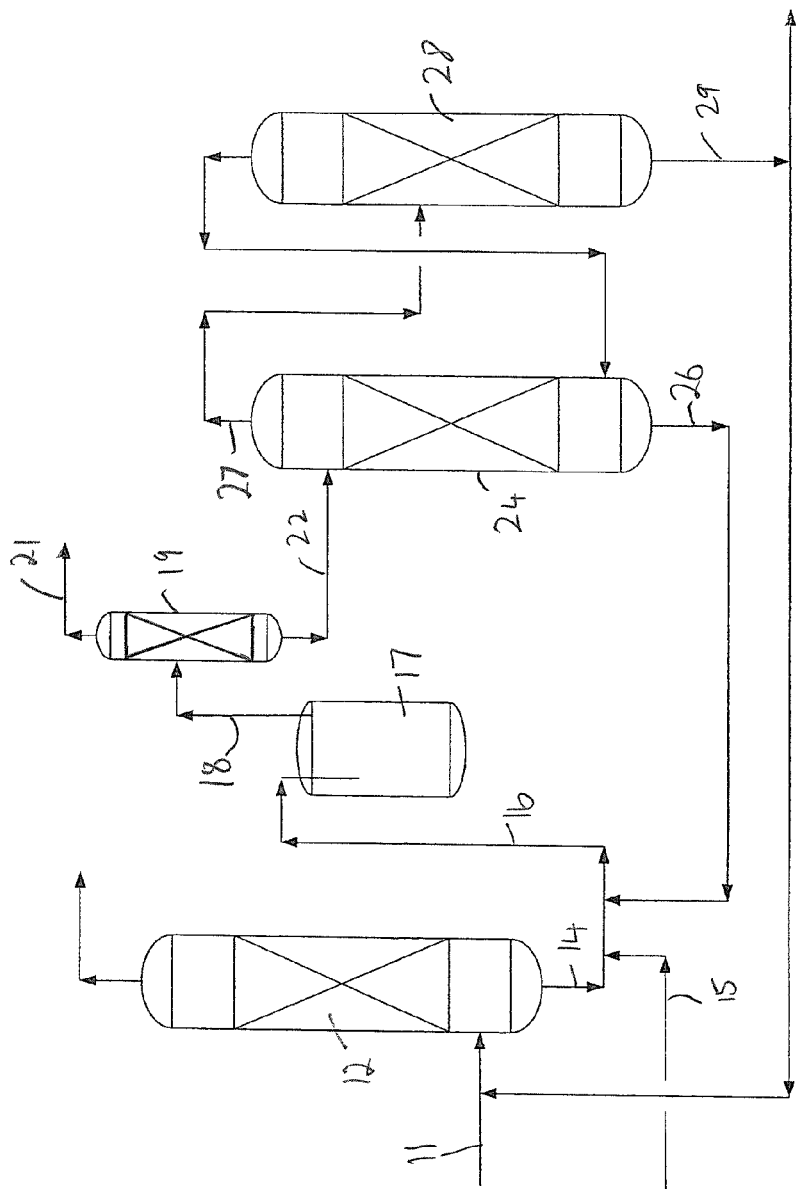
FIG. 3 is a flow diagram of a method according to a third example of the invention for recovering phenol and acetone from a BPA residue stream.

A third example is shown in FIG. 3, in which the supply line 23 for acid to neutralize the bottoms stream 22 is omitted so that the aqueous phase removed from the solvent extraction unit 24 via line 26 is alkaline and can be recycled to the hydrolysis reactor 17 to reduce the amount of fresh caustic that must be supplied to reactor 17 via line 15.

The following non-limiting Examples further illustrate the present process.

EXAMPLE 1

Residue Concentration

A residue stream was collected from a BPA manufacturing plant having the following composition: 75 weight percent phenol, 17 wt % bisphenol A and isomers thereof, and 8 wt % trisphenol and BPA heavies.

The residue stream was distilled to recover pure phenol as an overhead product and produce a concentrated bottoms stream that contained 50 wt % phenol, 34 wt % bisphenol A and isomers thereof, and 16 wt % trisphenol and BPA heavies.

A continuous reactor was operated at a temperature of 250° C. and a pressure of 500 psig (3550 kPa), in which 45 grams of the concentrated bottoms stream were mixed with 150 grams of an 8 wt % sodium hydroxide in water solution. In the reactor, 80% of the phenol and acetone in the bisphenol A and isomers thereof, trisphenol and BPA heavies were recovered.

EXAMPLE 2

Neutralization and Extraction

Acetone was recovered from the effluent of the continuous reactor used in Example 1 to leave a composite mixed phase stream containing phenol, unhydrolyzed heavies, and water. This mixed phase stream was fed at a rate of 50 grams an hour to the top of an extraction column along with 4 grams of concentrated sulfuric acid to convert sodium phenate to phenol. To the bottom of the extraction column, 55 grams of di-isopropyl ether were fed. Approximately 70 grams of an organic phase containing the ether extractant, phenol, and unhydrolyzed heavies was recovered from the overhead of the extractor. A neutralized aqueous phase of about 35 grams, which contained a total of less than 0.25 wt % phenol and unhydrolyzed heavies, was produced from the bottom of the extraction column.

EXAMPLE 3

Extraction and Phenate Recycle

In another experiment, 250 grams of the mixed phase stream employed in Example 2 were fed to the extraction column with 55 grams of di-isopropyl ether. For this experiment, no sulfuric acid was added to convert the sodium phenate to phenol. The aqueous stream, which contained sodium phenate and unhydrolyzed heavies and sodium salts thereof, was collected for recycle to the hydrolysis reactor.

The phenate containing aqueous stream was fed to the hydrolysis reactor at a rate of 150 grams per hour along with 45 grams per hour of the concentrated bottoms stream described in Example 1. Analysis of the reactor effluent showed that just over 70 percent of the phenol and acetone were recovered from the bisphenol A and isomers thereof, trisphenol and BPA heavies in the concentrated bottoms stream.

EXAMPLE 4

Phenol Recovery

The organic phase from Example 2 containing the extractant, phenol and unhydrolyzed heavies was fed at a rate of 245 grams per hour to a distillation column operating at atmospheric pressure and a bottoms temperature of about 200° C. The extractant, di-isopropylether, was recovered overhead at a tops temperature of about 70° C. at a rate of 160 grams per hour. A side draw was used to recover extractant-free phenol at a rate of 78 grams per hour. The remaining 7 grams, which contained about 8 wt % phenol, were recovered as heavies from the bottom of the column.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A method of treating a residue stream from the production of bisphenol-A, the method comprising:
   (a) contacting the residue stream with an aqueous solution of a base under conditions effective to hydrolyze at least part of said residue stream into acetone and phenol and produce an effluent stream;
   (b) recovering acetone from the effluent stream to produce a phenol-containing mixed phase stream which is substantially free of acetone and which contains water and unhydrolyzed heavy organic compounds;
   (c) treating the phenol-containing mixed phase stream with a water-immiscible organic solvent to extract phenol and unhydrolyzed heavy organic compounds into said solvent and produce an organic phase containing said solvent, phenol and unhydrolyzed heavy aromatic compounds and an aqueous phase with reduced concentrations of phenol and unhydrolyzed heavy organic compounds;
   (d) recovering at least part of the phenol and the organic solvent from the organic phase; and
   (e) purging at least part of the remaining unhydrolyzed heavy organic compounds.

2. The method of claim 1, wherein acetone is recovered from the effluent stream in (b) by distillation.

3. The method of claim 1, wherein at least part of the acetone recovered in (b) is recycled to the production of bisphenol-A.

4. The method of claim 1, wherein the water-immiscible organic solvent is selected from cumene, toluene, a mixture of cumene and alpha methyl styrene (AMS), ethers, ketones, and acetate esters.

5. The method of claim 1, wherein at least a portion of the aqueous phase produced in (c) is recycled to the contacting step (a).

6. The method of claim 1, wherein the phenol-containing aqueous stream from (b) is combined with an acid to reduce the pH of said stream to about 2 to about 8 prior to said treating step (c).

7. The method of claim 6, wherein the pH of the phenol-containing aqueous stream from (b) is reduced to about 5 to about 7 prior to said treating step (c).

8. The method of claim 1, wherein the recovering (d) is effected by one or more distillation steps.

9. The method of claim 1, wherein at least part of the phenol recovered in (d) is recycled to the production of bisphenol-A.

10. The method of claim 1, wherein at least part of the solvent recovered in (d) is recycled to the treating (c).

* * * * *